(12) United States Patent  
Westermann

(10) Patent No.: US 8,272,087 B2  
(45) Date of Patent: Sep. 25, 2012

(54) PIECE OF RESTING FURNITURE SUCH AS A BED OR CHAIR

(75) Inventor: Karsten Westermann, Sønderborg (DK)

(73) Assignee: Linak A/S, Nordborg (DK)

( * ) Notice: Subject to any disclaimer, the term of this patent is extended or adjusted under 35 U.S.C. 154(b) by 212 days.

(21) Appl. No.: 12/733,045

(22) PCT Filed: Aug. 11, 2008

(86) PCT No.: PCT/DK2008/000285  
§ 371 (c)(1),  
(2), (4) Date: Feb. 4, 2010

(87) PCT Pub. No.: WO2009/021513  
PCT Pub. Date: Feb. 19, 2009

(65) Prior Publication Data  
US 2010/0132117 A1    Jun. 3, 2010

(30) Foreign Application Priority Data  
Aug. 11, 2007 (DK) .................................. 2007 01147

(51) Int. Cl.  
 *A61G 1/00* (2006.01)
(52) U.S. Cl. .................................. 5/600; 5/613; 5/87.1
(58) Field of Classification Search .............. 5/600, 713, 5/718, 87.1, 81.1 R, 613, 618  
See application file for complete search history.

(56) References Cited

U.S. PATENT DOCUMENTS

| | | | |
|---|---|---|---|
| 4,934,468 A | 6/1990 | Koerber et al. | |
| 5,086,856 A | 2/1992 | Haggstrom | |
| 5,276,432 A * | 1/1994 | Travis | 340/573.4 |
| 5,410,297 A | 4/1995 | Joseph et al. | |
| 5,708,993 A * | 1/1998 | Campbell et al. | 5/86.1 |
| 5,780,798 A * | 7/1998 | Hall-Jackson | 200/85 R |
| 6,006,379 A * | 12/1999 | Hensley | 5/618 |
| 6,665,894 B2 | 12/2003 | Moffa et al. | |
| 6,718,572 B2 | 4/2004 | Schroeter | |
| 7,500,280 B2 * | 3/2009 | Dixon et al. | 5/713 |

FOREIGN PATENT DOCUMENTS

| | | |
|---|---|---|
| EP | 1634558 | 3/2006 |
| GB | 2390062 | 12/2003 |

OTHER PUBLICATIONS

English Abstract of EP1634558.

* cited by examiner

*Primary Examiner* — Fredrick Conley

(74) *Attorney, Agent, or Firm* — Dykema Gossett PLLC

(57) ABSTRACT

A piece of resting furniture such as a bed or chair comprising a least one actuator (4,5) and a control unit (11) and at least one control panel (9,10) to bring about an adjustment of the piece of furniture, and further comprising at least one strain gauge (18,19) connected to an alarm to detect whether a person is occupying the piece of furniture or not wherein the strain gauge (18,19) is located in connection with the actuator (4,5). The function is based on relative changes in the load on the strain gauge (18, 19) from a preset reference thereby allowing use of sensors with low resolution, which thereby are comparatively cheap. Moreover, when placing the strain gauge (18,19) in connection with the actuator (4,5) this simplifies the incorporation thereof in the piece of furniture. Not least the construction also renders it possible in an easy manner to upgrade existing hospital and care beds with an egress function.

20 Claims, 4 Drawing Sheets

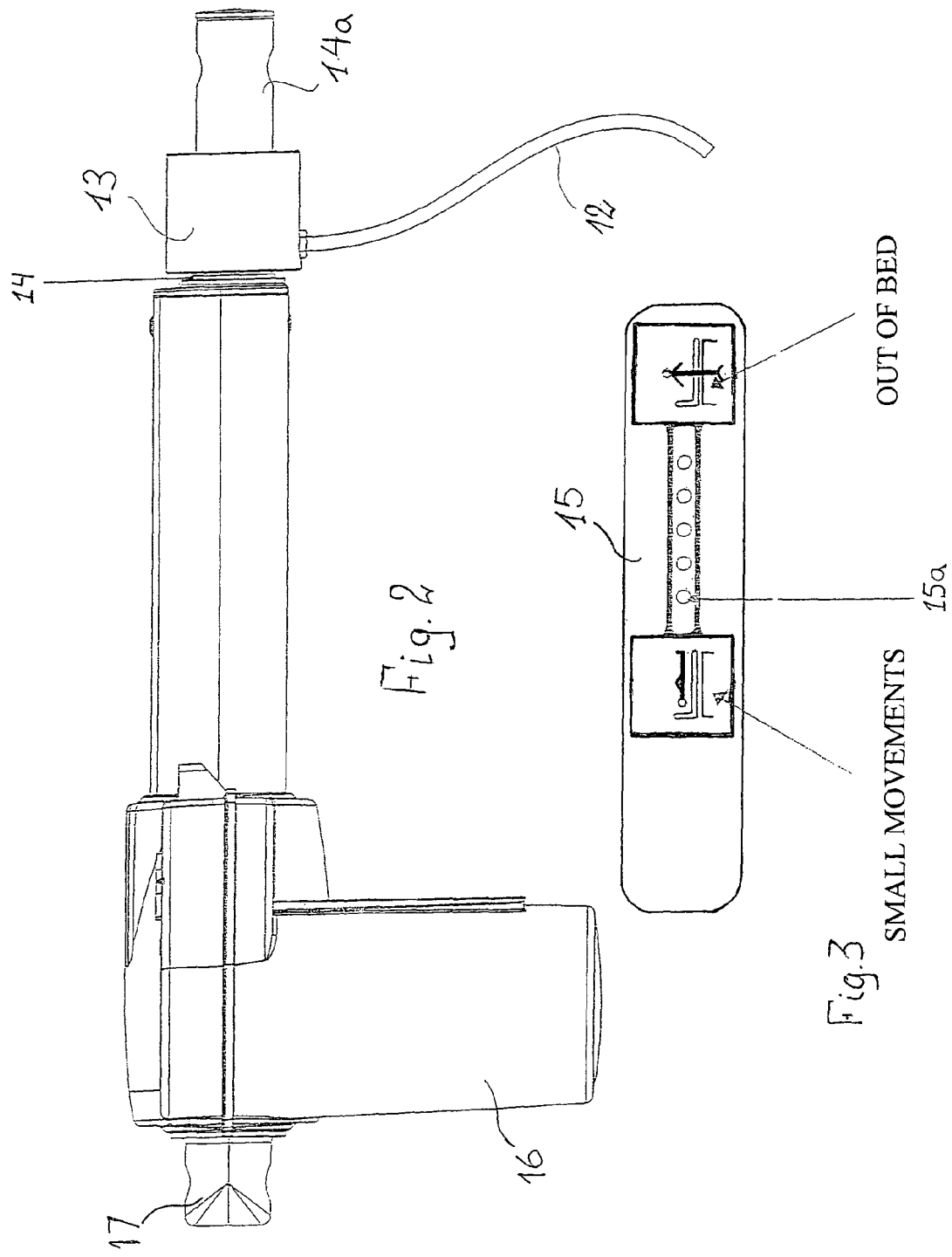

PIECE OF RESTING FURNITURE SUCH AS A BED OR CHAIR

BACKGROUND OF THE INVENTION

1. Field of the Invention

The invention relates to a piece of resting furniture such as a bed or chair. Further, the invention also relates to an actuator system applied in the furniture, and moreover the invention relates to a patient lift.

2. The Prior Art

The piece of resting furniture dealt with is of the nature which could be adjusted by means of at least one actuator. In hospital and care beds an upper frame carrying the mattress could be raised and lowered by means of actuators and also the back and leg rest of the support for the mattress could be adjusted by means of actuators. Also, leisure chairs in nursing homes could be adjusted by means of actuators. The types of actuators normally used is linear actuators with a thrust rod, see, e.g., WO 02/29284 A1 Linak A/S. A special linear actuator for beds is a double drive, see, e.g., WO 02/24035 A1 Cimosys A G. An example of a rotary actuators could be found in WO 01/17401 A1 Linak A/S designed especially for beds. For recliners or leisure chairs, linear actuators without a thrust rod, where the application is directly fixed to the spindle nut, are known (see, e.g., WO 96/12123 Koch sold by OKIN Gesellschaft für Antriebstechnik mbH).

In hospitals and nursing homes it is for some types of patients necessary for the nursing staff to know whether the patient is lying in the bed or is about to leave it (called pre-egress) or has left it (called egress). Such beds are among others described in U.S. Pat. No. 4,934,468 Hill Rom Co. Inc, and U.S. Pat. No. 5,276,432 Stryker Corp. In beds furnished with a weighing system for weighing and/or monitoring the weight of the patient, the weighing system could be employed for monitoring of the patient's position in relation to the bed. In such types of beds it is straight forward to incorporate an alarm in case the patient has left the bed. In more sophisticated elaborations it is also possible to detect if the patient is about to leave the bed or to detect the position of the patient in the bed. However, as such bed constructions basically are meant for weighing and/or monitoring weight of the patient, load cells with high resolution and of high quality are used, which also renders such constructions expensive. This means that such beds are only used within hospitals, and even finds restricted use, namely for patients requiring special treatments or special attention.

To improve care of patients on a general level in hospitals and nursing homes and to improve the working conditions for the staff, it would be helpful with a more widespread use of beds with at least an egress function.

Thus, it is an object of the invention to provide an egress function which makes it possible to implement in hospital or care beds on a larger scale.

SUMMARY OF THE INVENTION

This is achieved according to the invention by utilizing a strain gauge with the actuator in a piece of resting furniture. As the strain gauge should not weigh the patient or monitor the weight of the patient but exclusively should be used to detect whether a patient is resting in the piece of furniture or not, strain gauges of a very simple nature and with low resolution, and thereby relatively inexpensive strain gauges can be used. The egress function is based on relative changes in the load on the strain gauge from a preset reference, and if the changes exceed a predefined interval, then an audible or visual alarm is triggered. Moreover, when arranging the strain gauge in connection with the actuator, this simplifies the incorporation thereof in the piece of furniture. Going even a step further, mounting the strain gauge directly in or on the actuator makes it possible to supply a complete actuator system providing an egress function. This it possible in an easy manner to upgrade existing hospital and care beds with an egress function.

As the invention can provide an economical solution, this makes it possible to furnish ordinary hospital beds, care beds and leisure chairs with an egress function where it hitherto has not been the case for economical reasons.

In a preferred embodiment of the invention the actuator is an electromechanical linear actuator with a thrust rod which offers advantages as to the implementation of the strain gauge. This is especially true for the type of actuators where the forces is in a straight line between a front and rear mounting of the actuator, as, e.g., in WO 02/29284 A1 Linak A/S.

According to an embodiment of the invention, the strain gauge is mounted at the front end of the thrust rod, and in an alternative embodiment the strain gauge could also be mounted in connection with the rear mounting of the actuator. In a further elaboration of the invention the load cell, preferably at least one strain gauge, is located within the actuator in the line of forces between the front and rear mounting of the actuator. As the load cell is integrated in the actuator, this achieves the advantage that it should not be mounted separately. This of course means that the actuator should be manufactured accordingly.

In an embodiment, the strain gauge is arranged on the piece of furniture in connection with a bracket for mounting the actuator in the piece of furniture, since the line of forces fully flows through this part of the construction. This means that one basically could use a standard actuator.

Even though the preferred load cell component is a strain gauge where the read out will be a specific force measurement, it can be foreseen that other sensors can be used. Specifically, is here mentioned a piezoelement. Contrary to a strain gauge a piezoelement will only be able to indicate the dynamic change in the load and not a specific value. This puts special requirements on the control unit that has to calculate and determine if the egress signal meets the defined thresholds to indicate that the person has left the bed or is about to leave the bed.

The signal from the weighing cell, being a strain gauge or a piezoelement, varies since even the slightest movement of the person in the bed is recognized and amplified. If the person in the bed performs a quick movement, it could lead to a faulty indication of the person being on his way out of the bed. This problem is solved by continuously calculating a mean value on basis of a number of recent signals from the strain gauge, and the mean value is compared with a reference value, and in case the mean value falls without a preset value, then an audible or acoustic alarm is triggered. The reference value could be determined and set based on various criterion. In an embodiment the reference value is set when a patient is placed in the bed in a specific posture.

The sensitivity of the alarm can be set according to the state of the health of the patient. Rapid movements of the patient can be an indicator of bad sleeping quality or insufficient medication, which the service personal has to be aware of. If a patient under no circumstances is allowed to sit up in the bed or leave the bed, a high sensitivity setting will be able to call the service personal even before the patient has left the bed, thus hopefully enabling the service personal to prevent accidents from occurring.

Strain gauges are sensitive to environmental changes like the changing of the surrounding temperature, and needs calibration. This can be achieved by placing at least two identical strain gauges in the system, where no force is being applied to at least one of the strain gauges, thus giving a temperature depending signal that can be used to calibrate the readout from the stressed strain gauges in the system.

As a side effect to the functioning as a pre-egress and egress warning system, the strain gauges in addition can be used during operation of the actuators to indicate if the system is overloaded or blocked. This is brought about by measuring the applied force when adjusting the piece of furniture by reading the strain gauges, and if certain thresholds are met corresponding to an overload of the system, signalling can be made to stop the movement.

As to how to arrange the strain gauge in the bracket for mounting the actuator in the piece of furniture, the bracket has a hole where a bushing can be placed and kept in a fixed position in the hole. The bushing can be designed with an inlay of a number of strain gauges and of a dimensional stable material, preferably metal, and that the bushing is used for mounting one end of the actuator in the application. From both sides the hole in the bushing has a conical inlet that has its most narrow diameter in the mid length of the hole to shape a contact point between the bracket and a mounting rod such as a pin which serves to mount the actuator in the application. When a force is applied to the bushing inserted in the bracket, the strain gauges will be manipulated accordingly and an expression of the force applied can be read from the strain gauges. The bushing could be designed with an outer ring of a flexible material with an inlay of the number of strain gauges. In a system with two strain gauges, the strain gauges can be placed in the ring, so the first strain gauge will be manipulated when the activation member of the actuator is carrying a load where the second strain gauge is not manipulated by any force and can be used as a temperature reference signal as described earlier. In another situation the actuator will apply a force to the second strain gauge, where the first strain gauge will not be manipulated by any force thus being the strain gauge to be used as a temperature reference. Accordingly, it is possible to provide a system using only two strain gauges for measuring the push and pull forces of the actuator with a high accuracy of measurement since the strain gauge not being manipulated by any force can be used to provide a measure of the needed temperature compensation of the manipulated strain gauge. For an easy explanation the signal from the strain gauge can be separated into two parts: a fixed value which is temperature dependent and a dynamic part that reflects the force applied to the strain gauge. The value of interest is the dynamic part thus it would be the aim to isolate this value by compensating out the fixed temperature depending value. Practically the signals from the strain gauges can be fed through a differential amplifier, balancing out the contribution to the signal from the fixed temperature depending part. In this way, the output from the differential amplifier will reflect the force on the actuator mounting bracket with an indication of the direction of the force.

Having the strain gauges incorporated in the actuator itself in connection with a mounting bracket is a practical solution since the necessary electrical connections can be made inside the actuator. In addition, time can be saved installing the egress function in a bed since the function is built into the actuator component itself. According to an embodiment not only the connections for the strain gauges are integrated in the cabinet of the actuator itself, but also a unit connected to the strain gauges for receiving, amplifying, filtering and communicating the egress signal. It can be foreseen that parts of the circuit and cable network can be placed outside the cabinet. The connections between the strain gauges and the control is arranged in a way so that the strain gauges are connected to a control and communication unit within the cabinet of the actuator itself in order to forward the measurements on the strain gauges to an external control unit for processing the data and issuing alarms if certain conditions are met. It would on the other side not be a problem to integrate the full control system, the visible indications and transmitters for acoustic alarms directly in the cabinet of the actuator to form a stand alone egress warning system embedded in an actuator.

A control unit can be developed further to include various functions and controls. In one embodiment the control unit has means for recording a log representing the level of movement of the patient over time giving a picture of the state of the condition of the patient. In a further development a data processing of the log can be used to determine the state of: Quality of sleep, to tell if the medication is sufficient; The state of health represented by how physical active the patient is figured by no movement, slow movement or quick movement; Time in bed and out of bed; Position in bed and where in bed.

In resting furniture the back rest and/or the leg rest can be raised to various angle positions which influence the load on the actuators. It is an option to equip the actuators with a positioning system to detect the position of the movable element. E.g., in linear actuators it can be an absolute positioning system based on a potentiometer where the slider is locked to a spindle nut, the spindle nut moving over the travel of the spindle. Alternative solutions use hall sensors for counting the revolutions of one of the rotating parts in the actuator, where that number and the total number of revolutions over the travel of the spindle nut on its movement on the spindle can be used to calculate the position of the spindle nut and thereby the trust rod. This position information can be used in the egress system, in that the input from the strain gauges are calibrated with input from a positioning system, said positioning system giving the position of the spindle nut on its movement on the spindle and from this input determine the angle of the adjusted part of the piece of furniture, thus being able to calculate, from the angle and the resulting tension on the strain gauge placed in the line of forces through the actuator, the contribution of the weight of the patient resting on the part of the piece of furniture supported by the actuator.

When implementing the egress functionality in an actuator for raising or lowering an upper frame in respect to a lower frame, such as in a hospital or care bed, it must be taken into account that the upper frame is raised from contact with the lower frame, since a load change on the bed will not influence the strain gauge if the upper frame is resting on the lower frame. What is needed is that the load is carried by the actuator with the line of forces running through the mechanical parts measured by the strain gauge. This is very easily achieved by testing the position of the spindle nut in the actuator and accordingly adjusting the level of the upper frame until a gap is reached between the frames. If the actuator in which the strain gauge is incorporated is the actuator for adjusting the head or foot section of the bed, the same procedure can be used, testing the position of the spindle nut in the actuator and adjusting the head or foot section to be raised over the upper frame of the bed until a sufficient gap is achieved. Practically a raising angle of one or two degrees will be sufficient to create the necessary gap. If the head section is raised further in order for the patient to take a sitting position in the bed, the resulting force on the actuator that raises the head section applied by the weight of the patient will be proportional to the raising angle. Thus, the thresholds for when to activate the alarm must be calculated proportionally on the basis of the raised angle of the head section.

As the invention can provide an economical solution, this makes it possible to furnish ordinary hospital beds, care beds and leisure chairs with an egress function where it hitherto has not been the case for economical reasons and thereby provide a better caretaking and better working conditions for the attendant staff.

Further the invention also relates to an actuator system as applied in the furniture.

Having recognized the invention and bearing in mind that strain gauges could be used to measure a load, it is realized that the invention could be elaborated further in a patient lift to weigh a patient. The patient lift, according to the invention comprises a frame with a cantilever secured in a pivoting manner at its one end to a top end of the frame and its other end having means for carrying a patient and where the cantilever may be raised and lowered by means of a least one linear actuator with its one end attached to the frame and with its other end to the cantilever, and further comprises a control unit and at least one control panel, and comprising at least one strain gauge, the strain gauge being located in connection with the actuator and arranged to weigh the patient. In a patient lift the actuator will under normal operating conditions always be under pressure.

BRIEF DESCRIPTION OF THE DRAWINGS

The invention will be described more fully below with reference to the accompanying drawing, in which:

FIG. 2 shows an enlarged view of an actuator furnished with a strain gauge seen from above, FIG. 3 shows a display.

DETAILED DESCRIPTION OF THE PREFERRED EMBODIMENTS

Figure 1:
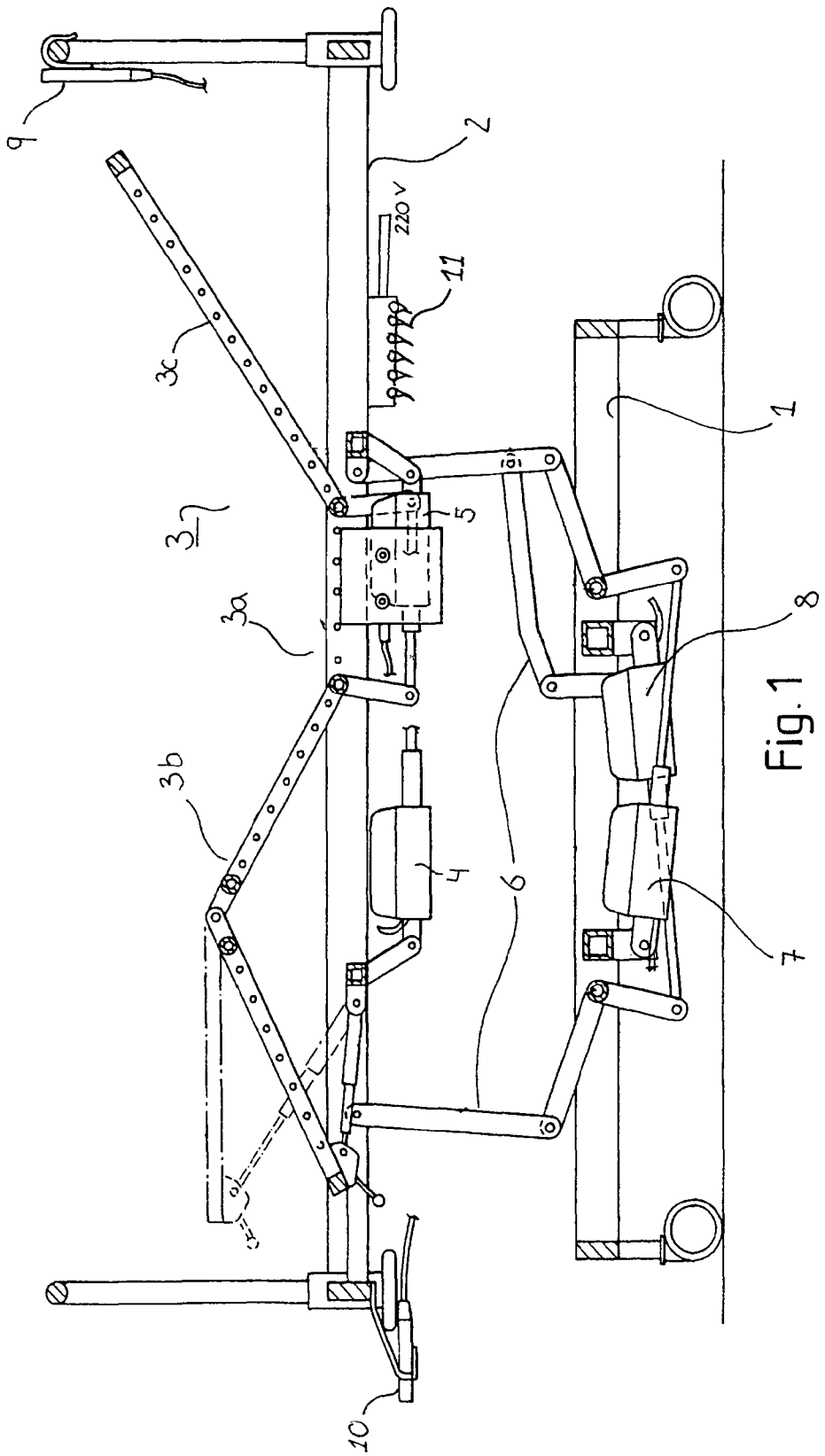
FIG. 1 shows a schematic side view of a hospital bed.

In FIG. 1 there is shown an adjustable hospital bed comprising a base 1 with wheels and an upper frame 2 with a support 3 for the mattress. The support has a middle portion 3a fixedly mounted in the upper frame 2 and an adjustable leg rest 3b and head rest 3c. The leg rest and head rest could be adjusted by linear actuators 4,5. The upper frame 2 is linked to the base 1 by a lever mechanism 6. The lever mechanism 6 is in the base 1 connected with two actuators 7,8 for raising and lowering the upper frame 2. The actuators are connected to a control unit 11 containing a power supply and an electric control circuit. The power supply consists of a low voltage unit, typically a transformer and rectifier, and a rechargeable battery pack used when the bed is out of range of a mains wall socket or in case of mains power failure. The patient could operate the bed by means of a wire connected remote control 9 at the head end of the bed. Further, or instead, there could be control panels integrated in side guards. The attendant could operate the bed with a wire connected remote control at the foot end of the bed. Further, or instead, there could be an operations panel 10 (ACP—Attendant Control Panel) which can be fitted to advanced hospital and care beds. It allows the nursing staff to retain direct control over critical functions. Such an operations panel could be of the type which could be drawn out from under the bed at the foot end. Just to mention it besides from being operated synchronously the two actuators 7,8 could also be operated individually to tilt the upper frame over a transverse axis (Trendelenburg/Anti-Trendelenburg position).

In the drawing FIG. 2 an upper view of a linear actuator is shown of the nature disclosed in the WO 02/29284 Linak A/S and reference is made thereto as part of the present specification. The end of the thrust rod 14 is equipped with a strain gauge in a housing 13, said housing comprises a first bowel shaped part attached to the end of the thrust rod and in said first bowel shaped part is located a strain gauge. Over the first bowel shaped part is placed upside down a second bowel shaped part such that the strain gauge is encaptured between two said bowel shaped parts. At the end of the second bowel shaped part is fastened a front mounting 14a for mounting the actuator in the bed structure. The load from the upper part of the bed including the weight of a patient would be transferred to the strain gauge via the front mounting 14a. The signal from the strain gauge is via the wire 12 transferred to an electronic signal handling equipment which in turn is connected with a control panel and an audible and/or visual alarm. The latter could be located in the attendants control room and connected to the computer system such that the alarm appears on a monitor together with an indication of the bed in question.

The electronic signal handling equipment is designed so that a mean value is calculated continuously on basis of a number of recent signals, e.g. the latest sixteen signals and in case this falls outside a preset value then the patient is just about to leave or has actually left the bed. When the patient is placed in the bed in the specific posture intended then the egress function is initiated by activating a key on the control panel. The sensitivity could also be set according to the state of the health of the patient. This is done by activating a key on the control panel having indicators for the sensitivity.

The control panel 15 is shown in FIG. 3 with a key at either end of an array of LED's there between. The icon on the key is indicating a bed and a person either on his way out of bed (to the right) or resting in the bed (to the left).

Figure 4:
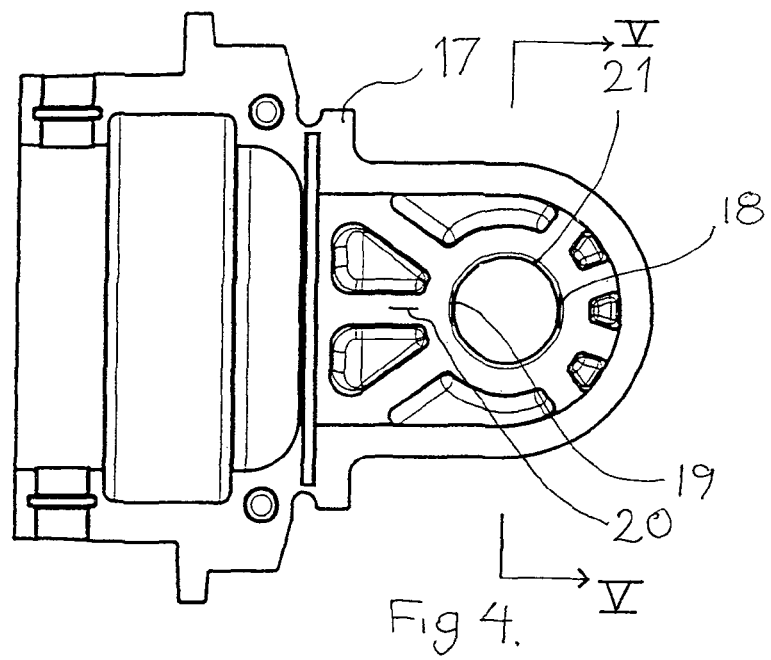
FIG. 4 shows a rear mounting bracket having a built-in strain gauge.
Figure 5:
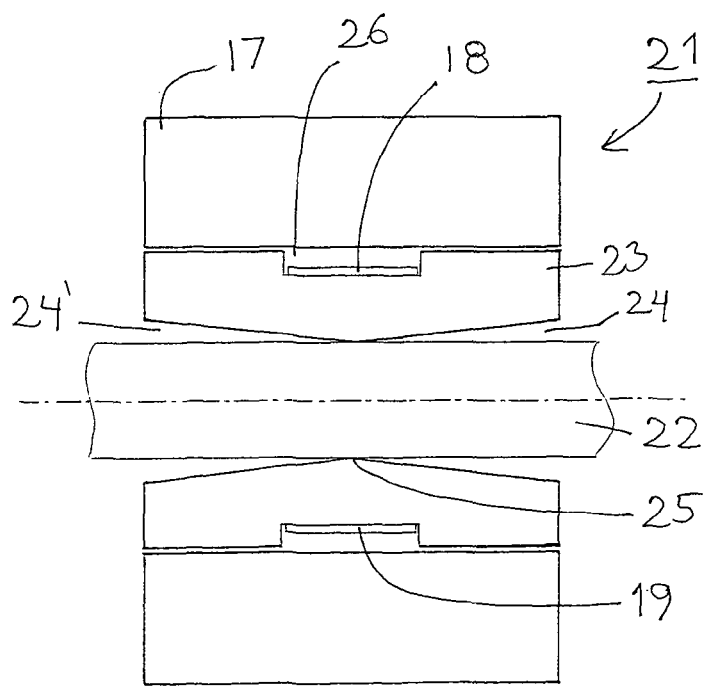
FIG. 5 shows a cross section of the rear mounting bracket in FIG. 4.

FIG. 4 shows a preferred embodiment of the invention where the strain gauges are mounted in connection with a rear mounting bracket 17 of the actuator. More specific, the strain gauges 18,19, are mounted directly in the bracket 17 for mounting the actuator in the piece of furniture. This is advantageous compared to the embodiment shown in FIG. 2, since the rear mounting bracket 17 of the actuator where the strain gauges 18,19 are incorporated is fixed in relation to the actuator cabinet 16. The wires (not shown in the drawing) for connecting the strain gauges 18,19 to the control unit 11 can therefore conveniently be lead directly through the cabinet 16. This makes the actuator with the strain gauges a compact and reliable unit where the cables are protected against wear and tear. In the actuator cabinet 16 the wires can be connected directly to a cable leading out of the actuator for processing the data outside of the actuator, typically in a control unit 11. Since the outputs from the strain gauges 18,19 are very sensible to electro magnetic noise, it would be preferred to amplify and filter the signals before forwarding the signals out of the actuator, and it can also be foreseen that the full egress functionality could be integrated in the cabinet 16 of the actuator itself, including the visual and audible indicators. As can be seen from the drawing, the strain gauges 18,19 are incorporated directly in the bracket in a ring-like arrangement 21 which in detail is shown in FIG. 5. The actuator is mounted in the piece of furniture by means of a pin 22. passing through a bushing 23 inserted in a hole of the rear mounting bracket 17. The bushing 23 is having conical inlets 24 from both sides, to form an access point towards the pin 22 in the mid 25 of the length of the bushing 23. On the outer side of the bushing 23 there is recess 26 in which the strain gauges 18,19 are mounted. When a pressure is applied on the rear mounting bracket 17, which could be caused by a load resting on the actuator's activation rod or if the actuator itself is activated to apply a force on the construction, the pressure will cause the bushing 23 to be compressed. The compression will be minimal since the bushing 23 is made of a form stable material, but the strain gauge 18,19 on the side of the bushing 23 having a force applied to it will be influenced and issue a signal proportional to the pressure. It is noted that strain gauges 18,19 are sensitive to temperature changes, and must be calibrated to temperature changes to reflect an exact applied pressure level. This calibration is done using the strain gauges 18,19 which is not under load. When the actuator is pushing the strain gauges 19 is under pressure whereas the strain gauges is relieved from any load and vice versa when the actuator exercises a pulling force. However the calibration can also be done by placing a further strain gauge 20 on a strain neutral place in the construction and using this strain gauge 20 as a temperature calibrated reference point to the strain gauges 18,19 placed in the line of force of the actuator.

It would be understood that either or both of the two actuators 4,5 raising and lowering the upper frame or either or both actuators 7,8 raising the head or foot section, could be equipped with a strain gauge as described above.

Further it would be appreciated that the invention is not restricted to the type of bed shown in the drawing. The invention could also be used in connection with beds where the upper frame is carried by a pair of actuators design as telescopic columns, e.g. as dealt with in WO 02/29284 A1 Linak NS. Also the invention could be used in leisure chairs, e.g. at nursing homes where an elderly person or a disabled person is placed in a leisure chair.

Figure 6:
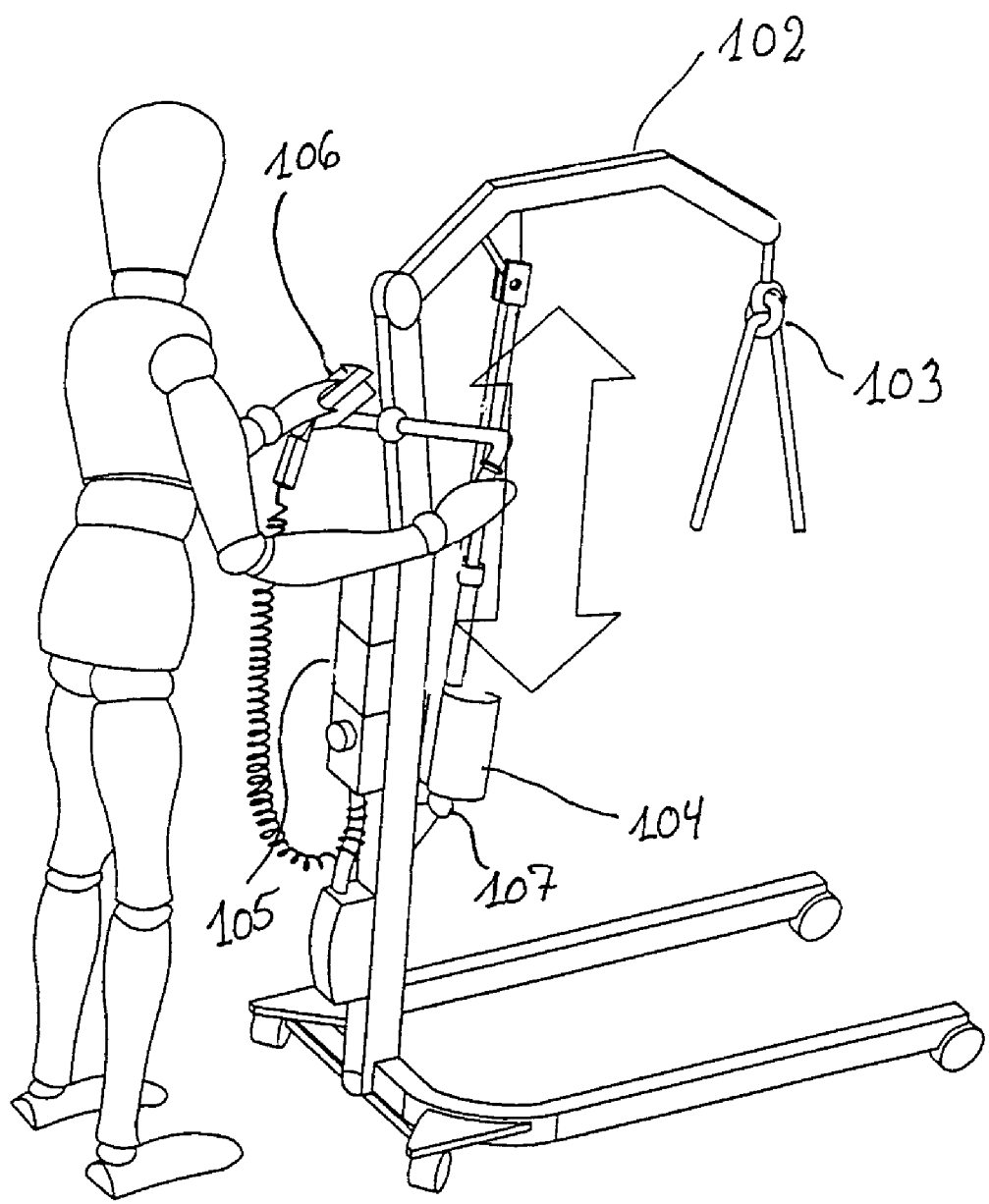
FIG. 6 shows a schematic picture of a patient lift.

In FIG. 6 there is shown a patient lift comprising a frame 101 provided with wheels. A cantilever 102 is secured at its one to the frame and is rotatable about a horizontal axis. A lifting hook 103 for lifting a patient is secured to the other end of the cantilever. The cantilever may be raised and lowered by a linear actuator 104, which is secured at its one end to the frame, and whose other end is secured to the cantilever. A control box 105 is mounted on the frame, containing a control unit and rechargeable batteries for operating the actuator. A handset 106 is connected to the control unit for maneuvering the cantilever. The rear mounting of the actuator 104 is furnished with a pair of strain gauges 18,19 arranged as described above and shown in FIGS. 4 and 5. However the strain gauges are arranged to weigh the patient and the patient's weight is read out on a display (not shown). In this context it would be understood that a high measuring accuracy is not required therefore non-expensive strain gauges could still be used.

The invention claimed is:

1. A piece of resting furniture which comprises:
   at least one electromechanical linear actuator with a thrust rod,
   a control unit,
   at least one control panel for adjusting the piece of furniture, and
   at least one strain gauge mounted at an end of the thrust rod and connected to an alarm for detecting whether a person is occupying the piece of furniture.

2. An actuator system as applied in the furniture according to claim 1.

3. A piece of furniture according to claim 1, wherein the control unit has means for recording a log representing a level of movement of the patient over time.

4. A piece of furniture according to claim 3, wherein the log can be used to determine:
   Quality of sleep (medication sufficient)
   State of health (no movement, slow movement, quick movement)
   Time in bed and out of bed
   Position in bed and where in bed.

5. A piece of furniture according to claim 1, wherein a load cell is located within the actuator in the line of forces between a front and rear mounting.

6. A piece of furniture according to claim 1, wherein the actuator includes a bracket and the at least one strain gauge is arranged on the piece of furniture in connection with the bracket.

7. A piece of furniture according to claim 1, wherein the strain gauge is a piezoelement.

8. A piece of furniture according to claim 1, wherein a mean value is calculated continuously on basis of a number of recent signals from the at least one strain gauge and said mean value is compared with a reference value and in case the mean value falls without a preset value then an audible or acoustic alarm is triggered.

9. A piece of furniture according to claim 8, wherein the reference value is set when a patient is placed in the piece of furniture in a specific posture intended.

10. A piece of furniture according to claim 9, wherein the sensitivity is set according to the patient's health.

11. A piece of resting furniture which comprises:
    at least one electromechanical linear actuator with a thrust rod,
    a control unit,
    at least one control panel for adjusting the piece of furniture, and
    at least one strain gauge mounted in connection with a rear mounting of the actuator and connected to an alarm for detecting whether a person is occupying the piece of furniture.

12. A piece of resting furniture which comprises:
    at least one electromechanical linear actuator with a thrust rod,
    a control unit,
    at least one control panel for adjusting the piece of furniture, and
    at least one strain gauge connected to an alarm for detecting whether a person is occupying the piece of furniture, said at least one strain gauge located within the actuator in a line of forces between a front and rear mounting of the actuator.

13. A piece of resting furniture which comprises:
    at least one actuator,
    a control unit,
    at least one control panel for adjusting the piece of furniture, and
    at least one strain gauge connected to an alarm for detecting whether a person is occupying the piece of furniture, wherein the at least one strain gauge is arranged on the piece of furniture in connection with a bracket for mounting the actuator in the piece of furniture, and wherein the bracket includes a hole wherein a bushing is placed and kept in a fixed position in the hole.

14. A piece of furniture according to claim 13, wherein the bushing is designed with an inlay of a number of strain gauges.

15. A piece of furniture according to claim 14, wherein the hole in the bushing from both sides has a conical inlet that has its most narrow diameter in a mid length of the hole, to shape a contact point between the mounting bracket and a mounting pin that serves to mount the actuator in the furniture.

16. A piece of furniture according to claim 15, wherein when a force is applied to the bushing inserted in the bracket, the at least one strain gauges will be manipulated accordingly and an expression of the force applied is read from the at least one strain gauge.

17. A piece of resting furniture which comprises:
at least one actuator,
a control unit,
at least one control panel for adjusting the piece of furniture, and
at least two identical strain gauges, at least one of said strain gauges being positioned at a location wherein no force is applied thereto, thus providing a temperature-dependent signal that can be used to calibrate readouts from other of said at least two strain gauges which are under stress.

18. A piece of resting furniture which comprises:
at least one actuator,
a control unit,
at least one control panel for adjusting the piece of furniture, and
at least one strain gauge connected to an alarm for detecting whether a person is occupying the piece of furniture, wherein a measurement of applied force is made when adjusting the piece of furniture by reading the at least one strain gauge, and if certain thresholds are met corresponding to an overload, signalling is made to stop movement.

19. A piece of resting furniture which comprises:
at least one actuator having a cabinet,
a control unit,
at least one control panel for adjusting the piece of furniture, and
at least one strain gauge connected to an alarm for detecting whether a person is occupying the piece of furniture, wherein the at least one strain gauge is connected to a control and communication unit within said cabinet in order to forward measurements on the at least one strain gauge to an external control unit for processing and issuing alarms if certain conditions are met.

20. A piece of resting furniture which comprises:
at least one actuator which includes a spindle and spindle nut,
a control unit,
at least one control panel for adjusting the piece of furniture, and
at least one strain gauge connected to an alarm for detecting whether a person is occupying the piece of furniture, wherein input from the at least one strain gauge is calibrated with input from a positioning system which provides a position of the spindle nut on the spindle and from this input determine an angle of an adjusted part of the piece of furniture, thus being able to calculate, from the angle and resulting tension on the at least one strain gauge placed in a line of forces through the actuator, a contribution of weight of a patient resting on the adjusted part of the piece of furniture supported by the actuator.

* * * * *